(12) United States Patent
Branam

(10) Patent No.: US 6,500,995 B1
(45) Date of Patent: Dec. 31, 2002

(54) WATER-ENHANCED PRODUCTION OF 1,1,1,3,3,-PENTACHLOROPROPANE

(75) Inventor: Lloyd B. Branam, Wichita, KS (US)

(73) Assignee: Vulcan Chemicals, Birmingham, AL (US)

( * ) Notice: Subject to any disclaimer, the term of this patent is extended or adjusted under 35 U.S.C. 154(b) by 0 days.

(21) Appl. No.: 09/880,010

(22) Filed: Jun. 14, 2001

(51) Int. Cl.$^7$ .............................................. C07C 17/30

(52) U.S. Cl. ....................................................... 570/257

(58) Field of Search ......................................... 570/257

(56) References Cited

U.S. PATENT DOCUMENTS

| | | |
|---|---|---|
| 3,346,651 A | 10/1967 | Moakes |
| 3,696,050 A | 10/1972 | Werts, III et al. |
| 3,862,978 A | 1/1975 | Decker et al. |
| 4,307,261 A | 12/1981 | Beard, Jr. et al. |
| 4,412,086 A | 10/1983 | Beard, Jr. et al. |
| 4,471,096 A | 9/1984 | Sharaby et al. |
| 4,480,121 A | 10/1984 | Klun et al. |
| 4,535,194 A | 8/1985 | Woodard |
| 4,542,231 A | 9/1985 | Dougherty et al. |
| 4,605,802 A | 8/1986 | Astrologes |
| 4,650,914 A | 3/1987 | Woodard |
| 4,803,009 A | 2/1989 | Gorski |
| 4,804,493 A | 2/1989 | Gorski |
| 4,961,870 A | 10/1990 | Cook et al. |
| 5,017,718 A | 5/1991 | Ojima et al. |
| 5,087,791 A | 2/1992 | Magistro |
| 5,569,794 A | 10/1996 | Tung |
| 5,574,192 A | 11/1996 | VanDerPuy et al. |
| 5,633,413 A | 5/1997 | Van Der Puy et al. |
| 5,683,554 A | 11/1997 | Brooks et al. |
| 5,696,310 A | 12/1997 | Jackson et al. |
| 5,792,893 A | 8/1998 | Wilson et al. |
| 5,902,914 A | 5/1999 | Rygas et al. |
| 6,040,487 A | 3/2000 | Baker et al. |
| 6,187,978 B1 | 2/2001 | Rygas et al. |

FOREIGN PATENT DOCUMENTS

| | | |
|---|---|---|
| DE | 1243172 | 6/1967 |
| DE | 2008617 | 10/1970 |
| DE | 2148185 | 4/1973 |
| EP | 1146463 | 3/1969 |
| EP | 0131561 A1 | 1/1985 |
| EP | 371821 A1 | 6/1990 |
| EP | 0729932 A1 | 9/1996 |
| FR | 2297213 | 8/1976 |
| GB | 1265567 A1 | 3/1972 |
| GB | 1265567 B | 3/1972 |
| JP | 46005289 B4 | 12/1971 |
| JP | 47011045 B4 | 4/1972 |
| JP | 48092310 | 11/1973 |
| JP | 50088007 | 7/1975 |
| JP | 06025027 A2 | 2/1994 |
| JP | 09183742 A2 | 7/1997 |
| JP | P200086545 A | 3/2000 |
| NL | 6602762 | 9/1966 |
| NL | 6609828 | 1/1967 |
| WO | WO 97/05089 A1 | 2/1997 |
| WO | WO 97/05090 A1 | 2/1997 |
| WO | WO 97/07083 A1 | 2/1997 |
| WO | WO 97/15540 A1 | 5/1997 |
| WO | WO 98/50330 A1 | 11/1998 |
| WO | WO 00/68172 A1 | 11/2000 |

OTHER PUBLICATIONS

CA 118:234530; Grishin, A. N. et al, "Process controlling of vinyl chloride polymerization in mass (suspension) with high degree of conversion"; Res. Inst. Polym. Chem. Technol., Dzerzhinsk, Russia) DECHEMA monogr., 127 (Int. Workshop Polym. React. Eng., 4th, 1992, 449–59 (English).

CA 109:151482; Sherman, A. M.; "Balancing formulation storage stability and cure behavior through the use of photoinitiator blends"; RADCURE '86, Conf. Proc., 10th, 4/13–4/25, Assoc. Finish. Processes SME:Dearborn, Mich. (English) 1986.

CA 102:181864; Klopman, G. et al; "Simple method of computing the partition coefficient"; J. Comput. Chem., 6(1), 23–28 (English) 1985.

CA 99:123046; Kolesnikov, V. Y. et al; "Kinetic methods for the control of vinyl chloride polymerization"; Plast. Massy (8), 7–8 (Russian) 1983.

CA 83:193849; Gladyshev, G. P.; "Control of vinyl chloride polymerization rate using weak initiators"; Plast. Massy (9), 73 (Russian) 1975.

CA 83:98026; Popov, V. A. et al; "Acceleration of the polymerization in bulk (suspension) of vinyl chloride at high degrees of conversion"; Vysokomol. Soedin., Ser. A. 17(6), 1226–8 (Russian) 1975.

Bellesia et al, *Synthetic Communications*, "The Fe$^0$ Promoted Addition of $CCl_4$ and $CCl_3Br$ to Olefins", 27(6), 961–971 (1997).

Zil'berman et al, *J. Organicheskoi Khimii*, "Synthesis of Liquid Telomers of Vinyl Chloride with Carbon Tetrachloride", vol. 3, No. 12, pp 2151–2156, Dec. 1967.

(List continued on next page.)

*Primary Examiner*—Alan Siegel
(74) *Attorney, Agent, or Firm*—Burns, Doane, Swecker & Mathis, L.L.P.

(57) ABSTRACT

A process is provided by which addition of water is used to enhance the production of any hydrochlorocarbon feedstock through the use of Kharasch chemistry, i.e. the combination of a polychlorinated alkane with an olefin to produce a chlorinated or hydrochlorinated alkane with the use of a transition metal compound in homogeneous solution as catalyst. Preferably, water is added to increase the production of 1,1,1,3,3-pentachloropropane by the reaction of carbon tetrachloride and vinyl chloride in the presence of a catalyst mixture of organo phosphate solvent, iron metal and ferric chloride.

12 Claims, 2 Drawing Sheets

OTHER PUBLICATIONS

Kotora, Martin et al, *Journal of Molecular Catalysis*, "Addition of tetrachlormethane to halogenated ethenes catalyzed by transition metal complexes", 77 (1) 51–60 (1992).

Kotora, Martin et al, *Institute of Chemical Process Fundamentals, Czech. Academy of Sciences*, Prague, React. Kinet, Catal. Lett., 44(2), 415–419 (1991).

Zhiryukhina et al, "Synthesis of Polychloroalkanes with Several Different Chlorine–Containing Groups", Inst. Elementoorg. Soedin. im. Nesmeyanova, Moscow, USSR, Izv. Akad. Nauk USSR, Ser. Khim. (1) 152–7 (1983).

Freidlina et al, "Reaction of gem–Trichloroalkanes with Unsaturated Compounds in Presence of $Fe(CO)_5$ and a Cocatalyst", Inst. Elementoorg. Soedin, Moscow, USSR, Izv, Akad. Nauk SSSR, Ser. Khim. (1), 174–7 (1977).

Upton C. J., et al; "Biomolecular Homolytic Substitution at Carbon. A Stereochemical Investigation", *J. Org. Chem*, vol. 41, No. 3, 523–530 (1976).

Onishchenko, T. A., et al, Catalysis of Telomerization of Vinyl Chloride With $Ccl_4$ by Some Iron Compounds and Effect of Adding $CH_3OH$, Inst. Elementoorg. Soedin, Moscow, USSR, Izv, Akad. Nauk SSSR, Ser. Khim. (8), 1770–5 (1972), Consultants Bureau, division of Plenum Publishing Corp, New York, NY.

Asahara, T., et cl; "Telomerization." II. N.M.R. analysis of telomers prepared from vinyl compounds and carbon tetrachloride. (Univ. Tokyo, Tokyo, Japan), Kogyo Kagaku Zasshi, 72(7), 1516–20 (1969.).

De Campto, F., et al, *Chem. Commun.*, "New and improved catalysts for transition metal catalysed radical reactions", pp 2117–2118, 1998.

Bellesia, F., et al, *Elsevier Science Ltd.*, "Telechelic oligomers by halogen atom transfer radical addition", *Tetrahedron*, 54(27), pp 7849–7856, 1998.

WATER-ENHANCED PRODUCTION OF 1,1,1,3,3,-PENTACHLOROPROPANE

BACKGROUND OF THE INVENTION

1. Field of the Invention

The present invention relates to a process for the manufacture of 1,1,1,3,3-pentachloropropane.

2. Description of the Related Art

The Montreal Protocol of 1987 placed a ban on certain substances that deplete the ozone layer, especially chlorofluorocarbons (CFC's). To hasten the elimination of CFC production and use, the Protocol allowed for certain fluorocarbon products (HCFC's) to be used as "bridge replacements." Although these bridge replacements are considerably more ozone friendly than CFC'S, they are intended to be transitional and not permanent replacements. Fluorocarbon producers are actively pursuing replacement candidates known as "third generation fluorocarbons." These third genera-tion fluorocarbons will require hydrochlorocarbon feedstocks.

The second largest U.S. fluorochemical end-use market, next to refrigeration, is for blowing agents utilized in the manufacture of various synthetic plastic formed products. CFC-1 1 was the dominant product in this market, however, it has been replaced by the bridge-fluorocarbon HCFC-141b. Because foam manufacturers must transition away from HCFC-141b by 2003, new third generation fluorocarbon products must be developed and commercialized.

Several fluorochemical producers have targeted fluorocarbon 1,1,1,3,3-pentafluoropropane, utilizing 1,1,1,3,3-pentachloropropane as the hydrochlorocarbon feedstock, as the primary replacement product for foam blowing applications. Zil'bennan et.al. ("Synthesis of liquid telomers of vinyl chloride with carbon tetrachloride", *J Org. Chem. USSR* (English Transl.), 3:2101–2105,1967)prepared 1,1,1,3,3-pentachloropropane in a 58% yield by the reaction of carbon tetrachloride and vinyl chloride using ferrous chloride tetrahydrate in isopropanol. In addition, Kotora et.al ("Addition of tetrachloromethane to halogenated ethenes catalyzed by transition metal complexes", *J Mol. Catal.*, 77(1):51–60,1992) prepared 1,1,1,3,3-pentachloropropane in high yields using either $CuCl/C_4H_9NH_2$ or $Ru(Ph_3P)_3$.

European Patent Application No. 131561 describes a very general process for the addition of a haloalkane to an alkene or alkyne compound in the presence of iron metal and a phosphorus(V) compound. While EP 131561 is very general in nature, several examples are set forth on the batch reaction of ethylene and carbon tetrachloride to produce 1,1,1,3-tetrachloropropane. However, EP 131561 does mention a wide variety of olefins and alkynes, including vinyl halides. EP 131561 also mentions that the batch process could be made continuous, but does not include any specifics on how this would be carried out.

Despite the known processes, improvements are needed in the manufacture of 1,1,1,3,3-pentachloro-propane. The present invention is directed to such an improved process. More particularly, the present invention relates to the addition of water to enhance production of 1,1,1,3,3-pentachloropropane.

OBJECTS AND SUMMARY OF THE INVENTION

It is an object of the present invention to provide an improved process for the production of chlorinated or hydrochlorinated alkanes. More particularly, a process is provided by which addition of water is used to enhance the production of any hydrochlorocarbon feedstock through the use of Kharasch chemistry, i.e., the combination of a polychlorinated alkane with an olefin to produce a chlorinated or hydrochlorinated alkane.

In one aspect, the invention provides a process for the production of a chlorinated or hydrochlorinated alkane by the reaction of a polychlorinated alkane and an olefin in a reactor, wherein water is added in an amount sufficient to increase the rate of the reaction.

In another aspect, the invention provides a process for the production of 1,1,1,3,3-pentachloropropane by the reaction of carbon tetrachloride and vinyl chloride in a reactor, wherein water is added in an amount sufficient to increase the rate of the reaction.

DESCRIPTION OF THE PREFERRED EMBODIMENTS

Figure 1:
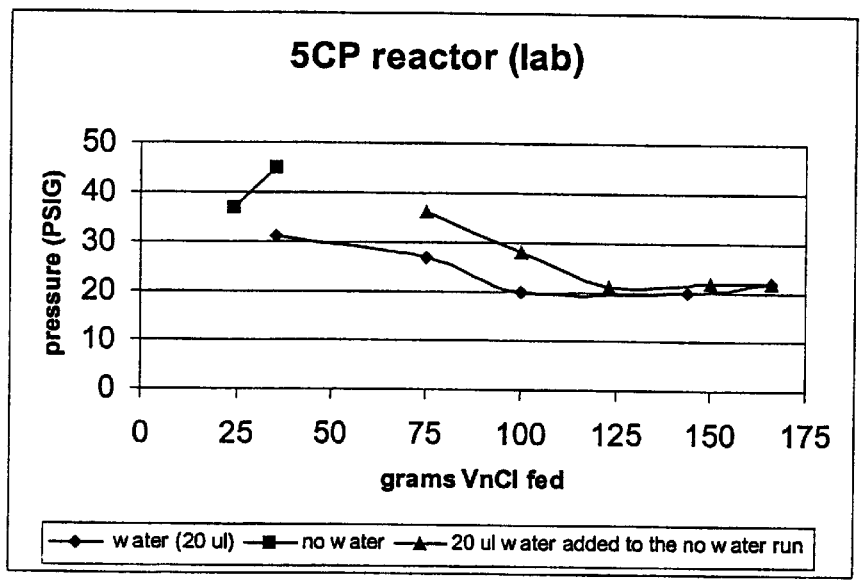
FIG. 1 illustrates the effect of water on 1,1,1,3,3-pentachloropropane production as a function of pressure versus grams of vinyl chloride fed.

The present invention generally relates to a process for the manufacture of the hydrochlorocarbon 1,1,1,3,3-pentachloropropane. More particularly, the present invention provides for the manufacture of 1,1,1,3,3-pentachloropropane by the reaction of carbon tetrachloride with vinyl chloride in the presence of tributyl phosphate solvent and a catalyst comprising metallic iron, ferrous chloride or ferric chloride and mixtures thereof, and enhanced production of 1,1,1,3,3-pentachloropropane by such a process upon addition of small amounts of water.

The present invention makes use of Kharasch chemistry for making 1,1,1,3,3-pentachloropropane (Kharasch et al, *Science*, 102:128, 1945). This chemistry involves combining a polychlorinated alkane with an olefin to produce a chlorinated or hydrochlorinated alkane having the chlorine in precise locations. Transition metal compounds in homogeneous solution are typically used as catalysts. For example, carbon tetrachloride may be added to ethylene in the presence of dissolved ferrous chloride and a cosolvent to make 1,1,1,3-tetrachloropropane with excellent selectivity.

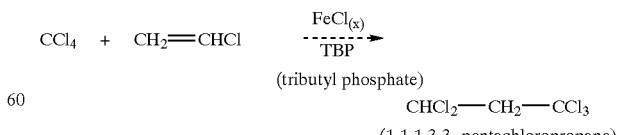

Thus, the present invention relates to the production or manufacture of 1,1,1,3,3-pentachloropropane by the liquid phase reaction of carbon tetrachloride with vinyl chloride. The catalyst is a mixture of ferrous and ferric chloride, with the ferrous chloride being generated by the reaction of ferric chloride and metallic iron in the presence of an organo phosphate solvent, such as tributyl phosphate.

The ferric/ferrous chloride catalyzed 1,1,1,3,3-pentachloropropane production is comprised of three processing steps: reaction, catalyst recovery, and purification. The reaction takes place in the presence of a ferric/ferrous chloride catalyst dissolved in organo phosphate solvent. Tributyl phosphate is the preferred organo phosphate solvent. The reaction is a Kharasch addition reaction in which a halogenated compound is added to the double bond of another compound. In this case, carbon tetrachloride is reacted with vinyl chloride to produce 1,1,1,3,3-pentachloropropane.

It has been observed that, at times, the reaction for production of 1,1,1,3,3-pentachloropropane is sluggish. During these sluggish periods, the reaction rates are slowed and the selectivity to desired products suffers. It has been found that addition of a small amount of water to the reactor results in a dramatic increase in the reaction rate of vinyl chloride and carbon tetrachloride and eliminates erratic operation. Water addition results in an exothermic reaction with good feed conversions and completion of the run with pressures well below the limitations of the production equipment.

This solution to the problem of sluggish production of 1,1,1,3,3-pentachloropropane is counter-intuitive since, prior to the present invention, the conventional wisdom has been to avoid addition of water during production of chlorinated hydrocarbons due to the possibility of corrosion. The ferric chloride used in the reaction would normally be expected to be deactivated by water and, thus, one would typically keep the feedstocks as dry as possible.

Water in any amount which enhances the rate of reaction of carbon tetrachloride and vinyl chloride to produce 1,1,1,3,3-pentachloropropane is within the scope of the present invention. Water is added in an amount ranging from about 1 ppm to about 500 ppm based on the total weight of the reactants. More preferably, a range of 10 ppm to about 50 ppm of water based on the total weight of the reactants is used. Water can be added to the reactor periodically or in a continuous fashion.

More generally, water addition can be used to enhance the production of any hydrochlorocarbon feedstock through the use of Kharasch chemistry, i.e., the combination of a polychlorinated alkane with an olefin to produce a chlorinated or hydrochlorinated alkane with the use of a transition metal compound in homogeneous solution as catalyst.

EXAMPLE 1

Laboratory Reactor Setup

A 1-liter glass reactor from ACE Glass capable of handling 50 psig was set-up in the laboratory. The reactor was fitted with an externally driven stirrer, a vent going to a manifold containing an emergency relief valve and rupture disk (50 psig), a thermowell, sample valve, and vinyl chloride addition tube extending below the reactor liquid level. The reactor was operated as a semi-batch system with all the ingredients (reactants and catalyst mixture) being added to the reactor at the beginning of a run except for the vinyl chloride. The vinyl chloride was metered continuously into the reactor through an FMI pump at a rate of approximately 1 gram/minute. For each run, the reactor was charged with iron (Fe) powder, ferric chloride ($FeCl_3$), carbon tetrachloride ($CCl_4$), and tributyl phosphate (TBP). Subsequent runs also included a charge of 1,1,1,3,3-pentachloropropane pilot plant flasher bottoms in order to simulate anticipated plant reactor conditions. The solution was mixed at 250 rpm and heated to 60° C. Initially, vinyl chloride (10 grams) was added to the mixture to prevent undesirable side reactions as the solution reached reaction temperature. When the solution reached the desired operating temperature of approximately 100° C., the vinyl chloride feed was introduced at a rate of 1 gm/minute. The temperature was controlled at 104° C. during the run. The vinyl chloride was fed from a reservoir on a balance in order to accurately measure the amount added during the run. The experimental run was allowed to operate an additional hour after the vinyl chloride addition was complete.

EXAMPLE 2

Baseline Runs, No Water Addition

The initial shake down runs were conducted with the following materials charged to or being fed to the reactor during the run.

| Compound | Weight(gms) | Weight Percent | Moles | Molar Ratio to Vinyl chloride |
|---|---|---|---|---|
| Vinyl chloride | 166.0 | 19.53 | 2.656 | |
| $CCl_4$ | 657.0 | 77.31 | 4.272 | 1.61 |
| TBP | 17.43 | 2.05 | 0.065 | 0.025 |
| $FeCl_3$ | 9.00 | 1.06 | 0.055 | 0.021 |
| Fe | .45 | 0.53 | 0.01 | 0.003 |

The $CCl_4$, TBP, $FeCl_3$, and Fe were added to the reactor, which was stirred at 250 RPM. After the temperature reached approximately 60° C., 10 grams of vinyl chloride were added to prevent unwanted side reactions as the solution approached operating temperature (104° C.). The remaining vinyl chloride was metered into the solution at approximately 1 gram/minute until the total weight desired for the experimental run had been added. The initial runs had to be stopped several times due to excessive pressure in the reactor and the run was terminated without being able to feed the desired amount of vinyl chloride. The rupture disk was set at 50 psig and the vinyl chloride addition was stopped when the pressure reached 45 psig. The next few runs were modified to try to increase the reaction rate and thus decrease the pressure of the system due to unreacted vinyl chloride. The modifications to the system included:

(1) Slower addition of vinyl chloride;
The vinyl chloride was added at a rate of approximately 0.7 grams/minute;

(2) Higher temperature (115° C.);

(3) Additional iron powder;
The amount of iron powder added to the reactor was doubled from the baseline amount;

(4) Addition of ferrous chloride in addition to the ferric chloride and iron powder;

(5) Addition of 1,1,1,3,3 pentachloropropane to increase the vinyl chloride solubility; 220 grams of pure 1,1,1,3,3 pentachloropropane was added to the reactor to adsorb more unreacted vinyl chloride and lower the vapor pressure of the reactant mixture which results in lower pressure in the reactor;

(6) Additional TBP;
The TBP was increased from 17.4 grams to 25 grams.

In every case, the experimental run had to be prematurely terminated due to excessive pressure.

EXAMPLE 3
Addition of Water

A run was completed with the addition of 20 micro-liters of water using the same feed material concentrations as a previous run, which had to be terminated due to excessive pressure:

| Compound | Weight (gms) | Weight Percent | Moles | Molar Ratio to Vinyl Chloride |
|---|---|---|---|---|
| Vinyl Chloride | 166.0 | 19.35 | 2.656 | |
| $CCl_4$ | 657.0 | 76.58 | 4.272 | 1.61 |
| TBP | 25.0 | 2.91 | 0.094 | 0.035 |
| $FeCl_3$ | 9.00 | 1.05 | 0.055 | 0.021 |
| Fe | 0.9 | 0.105 | 0.016 | 0.006 |

During this run, as the reaction temperature approached 104° C., there was a large exothermic reaction where the temperature increased 10–20° C. This was very surprising because the amount of water added was only an increase of 23-ppm in the system. In all the previous runs, no exothermic reaction was noted. This addition of a small amount of water also allowed this run to go to completion without exceeding the pressure limitations of the glass reactor.

EXAMPLE 4
Addition of Water

Example 3 was repeated using 10 micro-liters of water instead of 20 micro-liters with the same results. There was an exothermic reaction and the vinyl chloride was fed to the system at the desired rate and concentration without exceeding the pressure limitations of the glass reactor. Several attempts were made to control the exothermic reaction. Modification in the operating procedure included heating the mixture to 60° C. (versus 100° C.) and adding 10 grams of vinyl chloride, addition of 1,1,1,3,3-pentachloropropane to allow dilution of the reactants, and slower heating of the reactant mixture. The addition of 220 grams 1,1,1,3,3-pentachloropropane as a diluent was the most helpful in controlling the exothermic reaction.

EXAMPLE 5
Water Addition with Pilot Plant Flasher Bottoms

An experimental run was conducted whereby 20 micro-liters of water was added to the laboratory reactor after it had been charged with flasher bottoms from the pilot plant reactor. The flasher bottoms material was removed from the pilot plant because of very poor reaction kinetics and overall poor operation. The feed and catalyst concentrations for the run were the same as Example 3 except that 220 grams of flasher bottoms were added to the reactor. The reactor ran well and all the vinyl chloride was added at the appropriate rate (1 gram/minute).

This run was repeated using the same conditions without the addition of water. After 37 grams of vinyl chloride out of the target total of 166 grams had been added, the pressure had increased to 45 psig and the vinyl chloride feed was shut off and the run stopped. Twenty micro-liters of water were added to the vinyl chloride feed line and, as the pressure allowed, the vinyl chloride was fed slowly to the system. An exothermic reaction occurred after some of the water and fresh vinyl chloride had entered the reactor. The pressure began to drop which allowed the vinyl chloride to be added to the system at the normal rate of 1 gram/minute. The effect of the water addition both before the start of the run with the flasher bottoms and during the run is shown in FIG. 1.

As noted in FIG. 1, the run with 20 micro-liters of water added at the start of the run had a pressure of approximately 30 psig after 25 grams of vinyl chloride had been added. This pressure dropped to 22–23 psig by the end of the run as the vinyl chloride and the $CCl_4$ reacted. The run without 20 micro-liters of water had a pressure of approximately 40 psig after 25 grams of vinyl chloride had been fed. This run could not continue due to excessive pressure. After the addition of 20 micro-liters of water in the vinyl chloride feed line, the run was allowed to continue and the pressure profile looked very similar to the previous run, operating at 22–23 psig.

EXAMPLE 6
Pilot Plant Run with Water Addition

Figure 2:
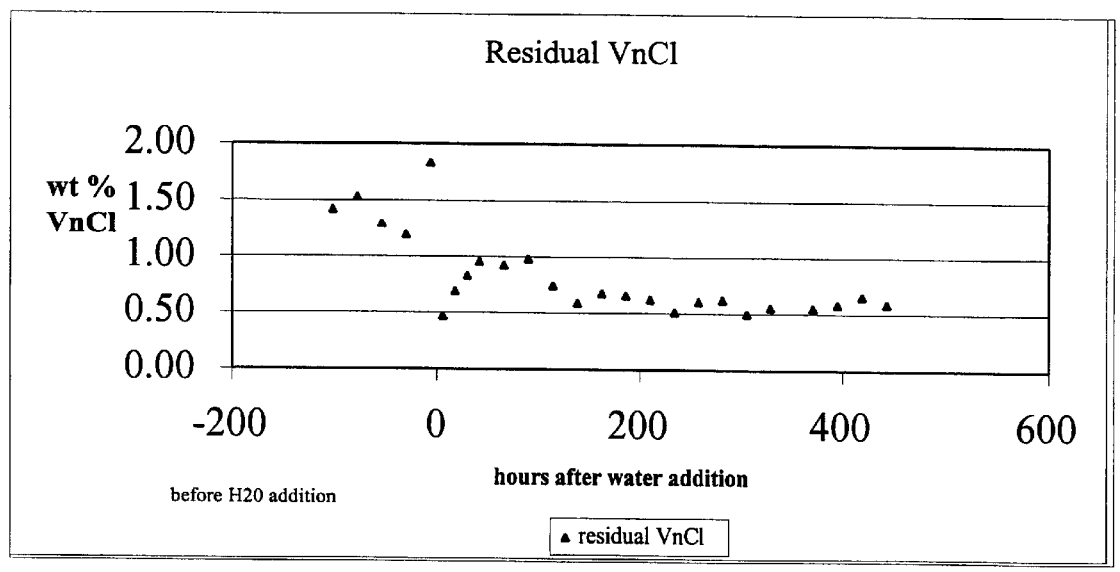
FIG. 2 illustrates the residual vinyl chloride after water addition in a process for making 1,1,1,3,3-pentachloropropane.
Figure 3:
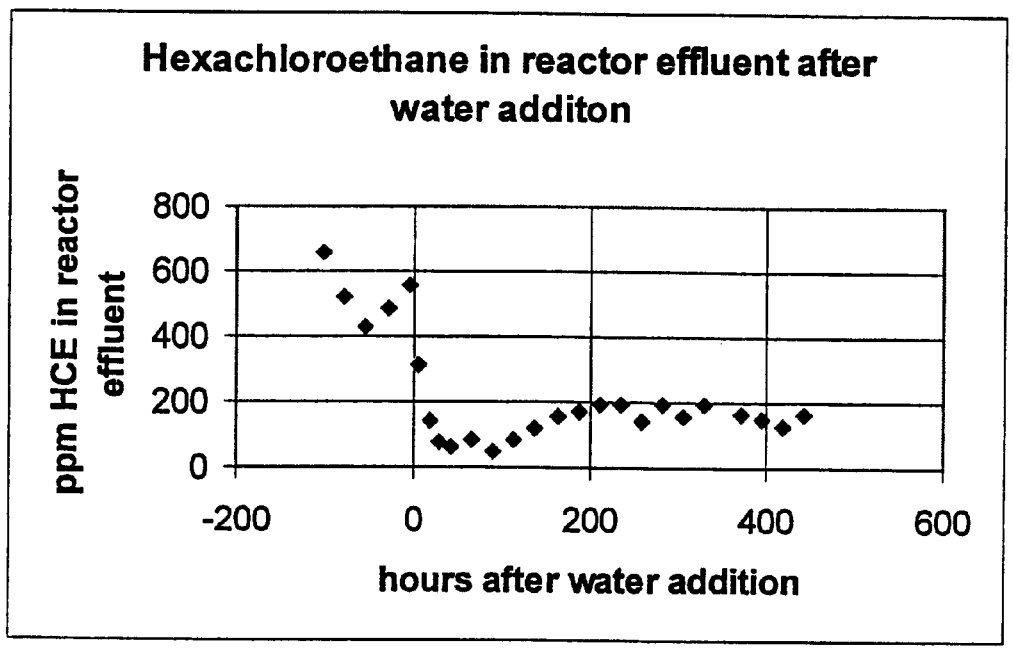
FIG. 3 illustrates the hexachloroethylene concentration in reactor effluent after water addition in a process for making 1,1,1,3,3-pentachloropropane.
Figure 4:
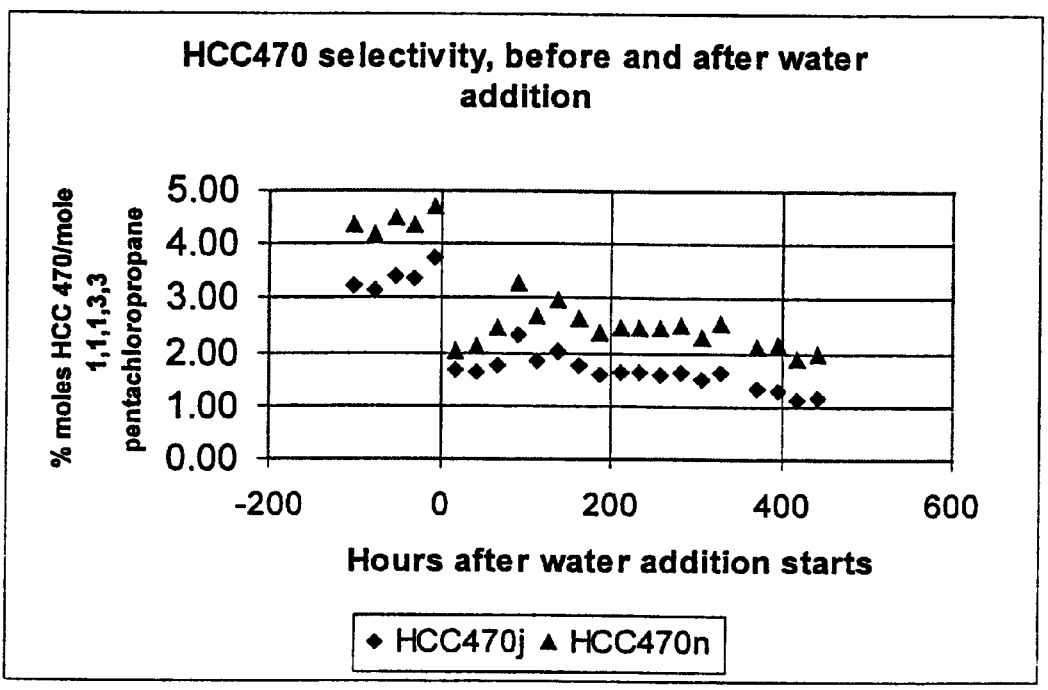
FIG. 4 illustrates the chlorinated pentane selectivity after water addition in a process for making 1,1,1,3,3-pentachloropropane.

The pilot plant process for producing 1,1,1,3,3-pentachloropropane had operated poorly for a significant period of time. Reaction rates were low and operating pressures high. The poor performance was attributed to operating with new batches of $CCl_4$ and TBP. The mixture of TBP and $CCl_4$ used in the catalyst addition system was spiked with water (65 ppm based on total reactants) and fed to the pilot plant reactor. The vent flows from the flash tower, which is mainly vinyl chloride, decreased dramatically during the next 4–6 hours. Also the vinyl chloride concentration in the reactor effluent decreased from 1.7 to 0.5 percent overnight. In addition to the decrease in vinyl chloride concentration (FIG. 2), the concentrations of waste by-products (hexachlorothane (FIG. 3) and chlorinated pentanes (FIG. 4) were also decreased.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A process for the production of 1,1,1,3,3-pentachloropropane by the reaction of carbon tetra-chloride and vinyl chloride in a reactor, wherein water is added in an amount sufficient to increase the rate of the reaction.

2. The process according to claim 1, wherein water is added at an amount ranging from about 10 ppm to about 50 ppm based on the total weight of the reactants.

3. The process according to claim 1, wherein the water is. added continuously or on a periodic basis.

4. The process according to claim 1, wherein the water is added directly to the reactor containing the carbon tetra-chloride and vinyl chloride.

5. The process according to claim 1, wherein the water is added to the carbon tetrachloride or vinyl chloride prior to their addition to the reactor.

6. The process according to claim 1, wherein the reactor contains a catalyst mixture comprising organo phosphate solvent, iron metal and ferric chloride.

7. The process according to claim 6, wherein the organo phosphate solvent is tributyl phosphate.

8. A process for the production of a chlorinated or hydrochlorinated alkane by the reaction of a polychlorinated alkane and an olefin in a reactor, wherein water is added in an amount sufficient to increase the rate of the reaction.

9. The process according to claim 8, wherein water is added at an amount ranging from about 10 ppm to about 50 ppm based on the total weight of the reactants.

10. The process according to claim 8, wherein the water is added continuously or on a periodic basis.

11. The process according to claim 8, wherein the water is added directly to the reactor containing the polychlorinated alkane and olefin.

12. The process according to claim 8, wherein the water is added to the polychlorinated alkane or olefin carbon prior to their addition to the reactor.

* * * * *